United States Patent
Duncan et al.

(10) Patent No.: US 10,799,208 B2
(45) Date of Patent: Oct. 13, 2020

(54) COMPRESSIONAL SOUND SPEED IMAGING USING ULTRASOUND

(71) Applicant: Siemens Medical Solutions USA, Inc., Malvern, PA (US)

(72) Inventors: David P. Duncan, Renton, WA (US); Yassin Labyed, Maple Valley, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 333 days.

(21) Appl. No.: 15/700,617

(22) Filed: Sep. 11, 2017

(65) Prior Publication Data

US 2018/0125451 A1 May 10, 2018

Related U.S. Application Data

(60) Provisional application No. 62/418,024, filed on Nov. 4, 2016.

(51) Int. Cl.
| | |
|---|---|
| *G01S 15/89* | (2006.01) |
| *A61B 8/08* | (2006.01) |
| *A61B 8/14* | (2006.01) |
| *G01S 7/52* | (2006.01) |

(52) U.S. Cl.
CPC ............... *A61B 8/08* (2013.01); *A61B 8/14* (2013.01); *A61B 8/5223* (2013.01); *G01S 7/52036* (2013.01); *G01S 7/52049* (2013.01); *G01S 7/52071* (2013.01); *G01S 15/8927* (2013.01)

(58) Field of Classification Search
CPC ........................................................ A61B 8/08
USPC ............................................................ 600/488
See application file for complete search history.

(56) References Cited

U.S. PATENT DOCUMENTS

| | | | | |
|---|---|---|---|---|
| 4,779,623 A | * | 10/1988 | Sumino | A61B 8/0858 600/440 |
| 6,490,474 B1 | * | 12/2002 | Willis | A61B 5/0422 600/424 |
| 2002/0099290 A1 | * | 7/2002 | Haddad | A61B 8/0825 600/443 |
| 2006/0074319 A1 | * | 4/2006 | Barnes | A61B 5/06 600/466 |

(Continued)

FOREIGN PATENT DOCUMENTS

WO    WO 2015091519    6/2015

OTHER PUBLICATIONS

Byram et al. "A method for direct localized sound speed estimates using registered virtual detectors." Ultrasonic imaging vol. 34,3 (2012): 159-80. doi:10.1177/0161734612455576 (Year: 2012).*

(Continued)

*Primary Examiner* — Amanda Lauritzen Moher
*Assistant Examiner* — Jillian K. McGough

(57) ABSTRACT

For sound speed imaging, different receive apertures are used instead of multiple transmissions from different angles. Acoustic echoes from a same transmission are receive beamformed with different apertures of the transducer array. The axial shift between the beamformed signals from the different apertures is used to solve for the speed of sound at one or more locations. The resulting measure of the speed of sound is displayed as the speed of sound in the tissue and may be diagnostically or prognostically useful.

16 Claims, 2 Drawing Sheets

(56) References Cited

U.S. PATENT DOCUMENTS

| | | | | |
|---|---|---|---|---|
| 2013/0144166 | A1* | 6/2013 | Specht | G01S 15/8913 |
| | | | | 600/441 |
| 2016/0317121 | A1* | 11/2016 | Frenz | A61B 8/08 |
| 2017/0128046 | A1* | 5/2017 | Kim | A61B 8/5207 |
| 2017/0188996 | A1* | 7/2017 | Kajiyama | A61B 8/4483 |
| 2017/0224308 | A1 | 8/2017 | Labyed et al. | |
| 2018/0132723 | A1* | 5/2018 | O'Reilly | A61N 7/02 |
| 2018/0271492 | A1* | 9/2018 | Jeon | G10K 11/346 |

OTHER PUBLICATIONS

Anderson, Martin E., and Gregg E. Trahey. "The direct estimation of sound speed using pulse—echo ultrasound." The Journal of the Acoustical Society of America 104.5 (1998): 3099-3106.

Imbault, Marion, et al. "Robust sound speed estimation for ultrasound-based hepatic steatosis assessment." Physics in Medicine and Biology 62.9 (2017): 3582.

Jaeger, Michael, et al. "Computed ultrasound tomography in echo mode for imaging speed of sound using pulse-echo sonography: proof of principle." Ultrasound in medicine & biology 41.1 (2015): 235-250.

Krucker, J. F., J. Brian Fowlkes, and Paul L. Carson. "Sound speed estimation using automatic ultrasound image registration." IEEE transactions on ultrasonics, ferroelectrics, and frequency control 51.9 (2004): 1095-1106.

Rosado-Mendez, Ivan M., Timothy J. Hall, and James A. Zagzebski. "Pulse-echo sound speed estimation based on a Nakagami model of the echo amplitude." Ultrasonics Symposium (IUS), 2014 IEEE International. IEEE, 2014.

Shin, Ho-Chul, et al. Estimation of speed of sound using medical ultrasound image deconvolution. Technical Report CUED/FINFENG/TR626, Cambridge University Engineering Department, 2009.

Wear, Keith A. "The dependence of time-domain speed-of-sound measurements on center frequency, bandwidth, and transit-time marker in human calcaneus in vitro." The Journal of the Acoustical Society of America 122.1 (2007): 636-644.

Wear, Keith A. "The effects of frequency-dependent attenuation and dispersion on sound speed measurements: applications in human trabecular bone." IEEE transactions on ultrasonics, ferroelectrics, and frequency control 47.1 (2000): 265-273.

* cited by examiner

COMPRESSIONAL SOUND SPEED IMAGING USING ULTRASOUND

RELATED APPLICATIONS

The present patent document claims the benefit of the filing date under 35 U.S.C. § 119(e) of Provisional U.S. Patent Application Ser. No. 62/418,024, filed Nov. 4, 2016, which is hereby incorporated by reference.

BACKGROUND

The present embodiments relate to speed of sound determination with ultrasound.

In ultrasound imaging, the speed of sound is assumed, such as assumed to be 1450 m/s. However, the speed of sound in tissue varies based on characteristics of the tissue. The speed of sound in a patient's tissue may be diagnostically informative.

Ultrasound tomography may be used to measure the speed of sound. Ultrasound tomography relies on placing the patient between a transmitter and a receiver. The travel time for acoustic energy from the transmitter to pass entirely through the patient to the receiver is used to calculate the speed of sound in the patient. Most ultrasound scanners use pulse-echo where the same transducer is used for transmit and receive operation, so speed of sound may not be estimated in the same way with pulse-echo systems. Speed of sound has been solved using computed ultrasound echo tomography (CUTE). Compressional sound speed is estimated or imaged by analyzing the relative axial displacement between beamformed images obtained from plane wave transmissions at different angles. This approach requires multiple transmissions, causing delay and making the process sensitive to background motion. The approach also uses plane waves, resulting in worse signal-to-noise ratio.

SUMMARY

By way of introduction, the preferred embodiments described below include methods, computer readable media, and systems for sound speed imaging. Instead of multiple transmissions from different angles, different receive apertures are used. Acoustic echoes from a same transmission are receive beamformed with different apertures of the transducer array. The axial shift between the beamformed signals from the different apertures is used to solve for the speed of sound at one or more locations. The resulting measure of the speed of sound is displayed as the speed of sound in the tissue and may be diagnostically or prognostically useful.

In a first aspect, a method is provided for sound speed imaging. A transducer array of elements of an ultrasound scanner transmits acoustic energy into tissue of a patient. At least first and second sub-apertures of the transducer array receive acoustic echoes responsive to the transmitting. The first sub-aperture is formed of a different grouping of the elements than the second sub-aperture. For different locations, axial displacements of signals from the received acoustic echoes of the first sub-aperture relative to signals from the received acoustic echoes of the second sub-aperture are estimated. Speed of sound is tomographically solved at each of the locations from the relative axial displacements. An image of the speed of sound is generated.

In a second aspect, a system is provided for imaging speed of sound. A transmit beamformer is configured to generate acoustic energy. A receive beamformer is configured to detect first and second receive beams in response to the acoustic energy. The first and second receive beams represent a same location. The first receive beam is formed from a different aperture on a transducer array than the second receive beam. An image processor is configured to determine a spatial or temporal shift for the location based on comparison of the first receive beam to the second receive beam and configured to calculate the speed of sound in the tissue at the location based on the shift. A display operable to display the speed of sound.

In a third aspect, a method is provided for imaging speed of sound. A transmitted field is generated with a transducer array of an ultrasound system. Scattered waves from the transmitted field are recorded with multiple spatially overlapped receive sub-apertures of the transducer array. Multiple sets of beamformed data are formed from the scattered waves for the multiple spatially overlapped receive sub-apertures, respectively. Relative axial spatial or relative temporal displacements between the multiple sets of the beamformed data are estimated. Speed of sound is calculated from the displacements. An image of the speed of sound is displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Compressional sound speed is estimated using pulse-echo scanning. Relative axial displacements between beamformed data obtained from overlapping receive apertures in response to a same transmit are calculated. The relative displacements are caused by the differences of the speed of sound of the medium compared to the beamforming speed of sound. The speed of sound is computed from the relative axial displacements.

Using the multiple receive sub-apertures, focused transmit may be used instead of plane waves. As a result, higher signal-to-noise ratio is provided. For a given location, a single transmit is needed instead of multiple transmissions. As a result, the speed of sound calculated for a given location is immune to background motion. For a given location, the speed of sound is estimated more quickly by using fewer transmissions.

The speed of sound is an acoustic parameter used to characterize tissue. The speed of sound provides quantitative information about the tissue being examined. The speed of sound may become a biomarker for some tissue pathologies, such as fatty liver disease. Sound speed estimates add another diagnostic dimension to the estimation of fat fraction estimation useful in liver or other applications. Sound speed images may be shown to the user as a new diagnostic confidence tool. Rather than correcting for aberration from shifts caused by differences in speed of sound, the calculated speed of sound may be used as a first order aberration correction for improving basic image quality.

Figure 1:
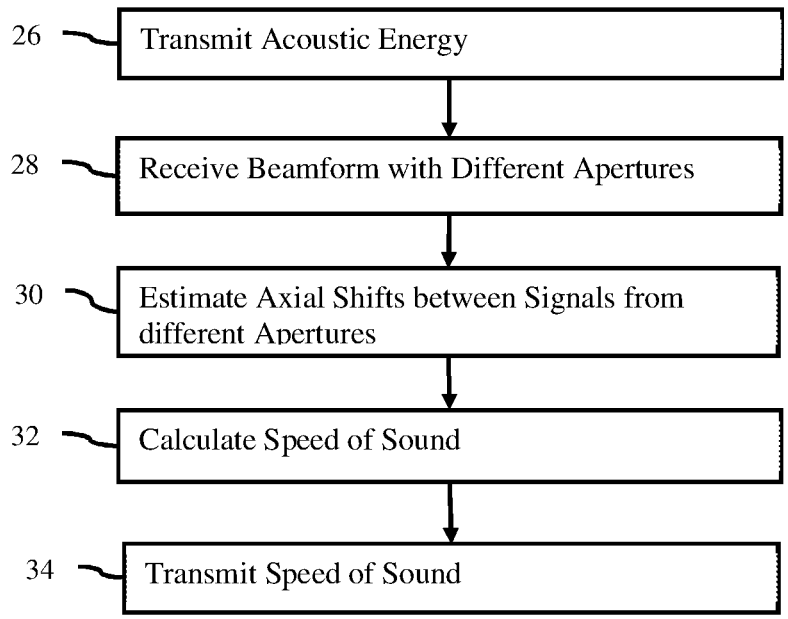
FIG. 1 is a flow chart diagram of one embodiment of a method for sound speed imaging.

FIG. 1 shows one embodiment of a method for sound speed imaging. An ultrasound scanner transmits acoustic energy and forms receive beams with different apertures in response to scattering of the acoustic energy. The axial shifts in the different receive aperture, receive beams at different locations are used to solved for the speed of sound at one or more of the locations. The calculated speed of sound may then be used for diagnostic or prognostic purposes, such as displaying a bulk speed of sound for a tissue region or showing spatial distribution of speed of sound in tissue of the patient.

Figure 3:
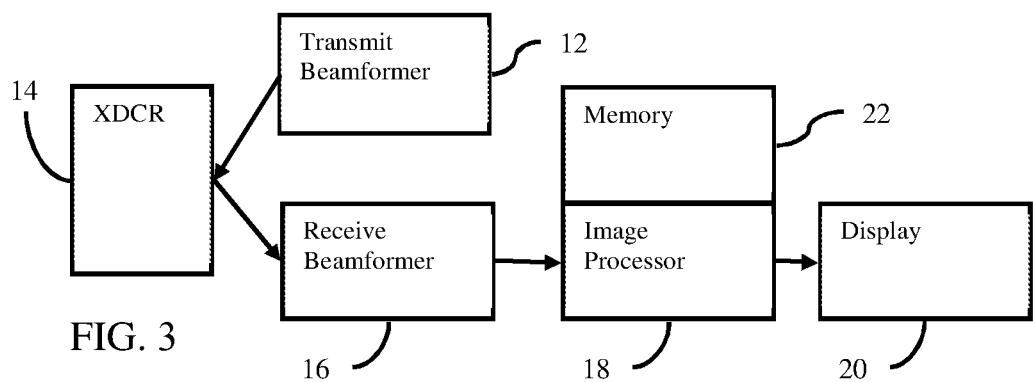
FIG. 3 is one embodiment of a system for estimating speed of sound in tissue.

The method is implemented by the system of FIG. 3 or a different system. For example, any now known or later developed ultrasound scanner performs the acts. An image processor of the ultrasound scanner performs acts 30-32. Alternatively, an image processor of a computer or workstation separate or remote from the ultrasound scanner performs any one or more of acts 30-32. Beamformers, memory, and/or other devices may be used to acquire the data using acts 26 and 28. The ultrasound scanner, image processor, display, and/or other device may perform act 34. The image processor may control the devices to perform the method of FIG. 1.

Additional, different, or fewer acts may be provided. For example, the method is performed without transmitting the speed in act 34. In another example, aberration is corrected by re-beamforming or beamforming for later scans using the calculated speeds of sound rather than a default or assumed speed. In other examples, filtering or other data processing is applied to the beamformed signals, displacements, and/or calculated speeds over time and/or space.

The acts are performed in the order described or shown (e.g., top to bottom or numerical), but may be performed in other orders. For example, act 26 shows transmission of a single excitation pulse. Act 24, and the responsive acts 28, 30, and 32 may be repeated to measure over a larger region of interest.

In act 26, an ultrasound scanner transmits acoustic energy into tissue of a patient. The transmit beamformer generates electrical waveforms. The transducer array 14 of elements in an ultrasound scanner transmits acoustic energy converted from the electrical waveforms. The acoustic energy is transmitted to the tissue in a patient. A transmitted field of acoustic energy is generated in the patient.

The transmission is a transmit beam focused at a depth or range of depths on a scan line. The focal depth is on the transmit scan line and may be within a region of interest. Alternatively, an infinite focal depth is used for generating a plane wave. A diverging wave throughout the region of interest may be generated in other embodiments.

Figure 2:
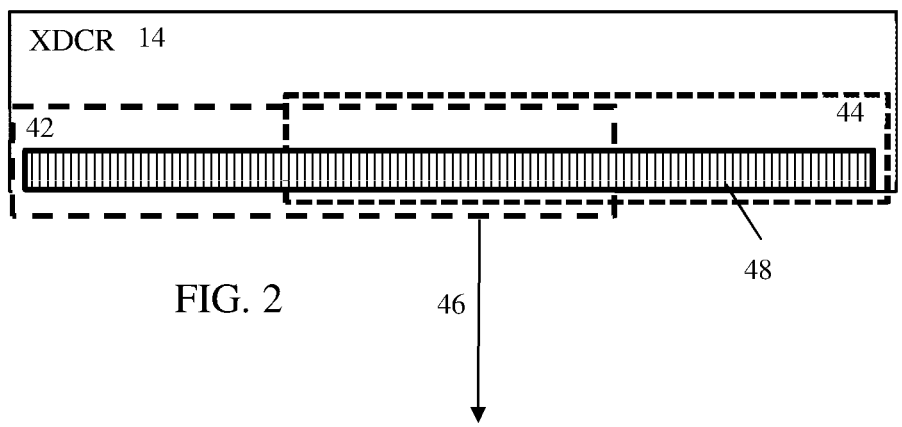
FIG. 2 illustrates an example transducer array with different receive apertures.

Based on a delay profile for the elements of the transducer, the transmit beam is transmitted along a transmit scan line. The scan line is at any angle to the transducer, such as normal to the transducer. FIG. 2 shows an example transmit scan line 46 from the transducer array (XDCR) 14. For a plane wave or diverging wave, the scan line 46 may represent an angle and/or center of the transmitted field where the acoustic energy is distributed to form receive beams over any number of receive scan lines, such as sampling an entire field of view or region of interest in response to one transmission. The point of origin of the transmit scan line 46 on the transducer 14 is the center of the transducer array 14, but may be offset from the center. The transmit aperture (i.e., elements 48 of the transducer array 14 used to generate the acoustic energy) may include all the elements 48 or may be a sub-set of the elements 48.

In act 28, a receive beamformer forms multiple sets of beamformed data. In response to the transmitted acoustic energy, acoustic echoes are generated. Some of the scattered waves of the acoustic echoes return to the transducer array. The elements of the transducer array convert the impinging scattered acoustic energy into electrical waveforms. By applying relative delays and/or phasing to different channels or electrical waveforms for different elements and summing the results across a receive aperture, a beamformed sample representing a location is formed. By altering the relative delays and/or phasing, beamformed samples along a receive scan line are formed, creating a set of beamformed data with dynamic receive focusing.

The beamformed data is in a radio-frequency (RF) format or an in-phase and quadrature (IQ) format. Other formats preserving phase information may be used. The channel data is combined into beamformed data, which is used prior to detection for calculating the speed of sound.

One receive beam is formed per receive aperture. For other scan lines, the transmit and receive operations are repeated. Beamformed data for other receive scan lines distributed in two or three dimensions within the patient may be formed with further transmit and receive operations. In other embodiments, any number of simultaneous receive beams may be formed per aperture, such as four, eight, sixteen, thirty-two, sixty-four, or more. Simultaneous receive beamformation and corresponding transmits may be used to scan a region of interest. In one embodiment, a parallel receive beamformer forms beams to sample the entire region of interest in response to a single transmit operation, such as in response to a plane wave or diverging transmit.

For calculating the speed of sound by location in the one, two, or three-dimensional region of interest, parallel receive beamformation with different receive apertures is used. The apertures are sub-apertures of the transducer array (i.e., each aperture is less than all the elements of the transducer array). FIG. 2 shows two receive apertures 42, 44. Two or more, such as four, receive apertures may be used.

The receive apertures are formed by different groups of elements 48 of the transducer array 14. The receive apertures 42, 44 may overlap, such as sharing some but not all elements 48. Any amount of overlap may be used, such as sharing half of the elements 48 of the transducer array 14. The electrical waveforms generated by the shared elements are used in beamforming for both receive apertures. In other embodiments, none of the elements 48 are shared (i.e., the receive apertures do not overlap). The elements 48 of each aperture 42, 44 are continuous, but intermittent (e.g., every other) groupings of elements 48 may be used.

Each aperture is used to form one or more receive beams. For a given scan line, a receive beam is formed from each of the receive apertures. Sets of beamformed data are provided for each receive scan line. The receive beams from different receive apertures are formed in response to the same or given transmit event and represent the same locations.

Each receive aperture forms one or more receive beams in response to a single or given transmit operation. As a result, for one or more locations, beamformed samples responsive to the same transmission of acoustic energy but from different receive beams are created. The locations and corresponding scan lines are distributed in one, two, or three dimensions. Two (or more) sets of beamformed data (RF of IQ) are generated from the respective two (or more) receive subarrays for each spatial location of interest. The scattered waves from the single transmit are recorded along a transducer array using multiple spatially overlapped receive sub-apertures. The electrical waveforms generated from the scattered waves of a given transmission are used to create multiple beamformed samples for each location in a region of interest from respective multiple different receive apertures.

In act 30, the image processor estimates relative axial spatial or temporal displacements between the multiple sets of the beamformed data. Along an axial dimension, displacement or shift in space corresponds to or is also a displacement or shift in time. Due to errors in beamforming sound speed, the scattered signals from a particular location to the different receive apertures appear shifted in time or in space. The axis is along the scan line (e.g., transmit and/or receive scan line 46) extending from the transducer array 14 at any angle from the transducer array 14. The beamformed samples are formed along the scan line, so data is provided at least along the axis of the scan line.

Since multiple sets of beamformed data are provided by the multiple receive apertures, the shift for each or some of the locations is determined. The shift is of one set relative to another set. For a location, three or more samples (i.e., axial window) from one receive aperture are compared to the samples of the other receive aperture. The samples from one set of beamformed data for a location are shifted axially by different amounts and compared to the beamformed data for another set. At each relative axial position, the similarity is measured. The spatial or temporal offset resulting in a best match provides the shift. The shift is immune to patient or transducer motion since the same transmit and receive operations are used to form the samples for the different receive apertures.

Any measure of similarity may be used for the comparison. In one embodiment, a cross-correlation is used. Other correlations may be used. The minimum sum of absolute differences may be used. The similarity is measured along the axial axis or along the scan line (e.g., axially cross-correlating), but other axes and/or two or three-dimensional shift may be measured.

Shifts may be found for different locations using different axial windows. Different locations may be associated with the same or different amount of shift. For each location of interest, the relative axial displacement of signals from the received acoustic echoes of one receive aperture with signals from the received acoustic echoes of the other receive aperture are estimated. Relative axial displacements (or time shifts) are estimated between the multiple datasets for one or more of the locations represented by both.

In act 32, the image processor calculates the speed of sound from the displacements. The shift at a given location is due to differences in the acoustic path formed by the different receive apertures, and to inaccurate beamforming sound speed. The difference in path due to spatially offset apertures subjects the acoustic energy to tissues with possibly varying sound speed. Since the shift measure for each location is a result of a sum of the differences in sound speed, tomographic reconstruction may be used. A field of shifts or displacements may be fit to a model of sound speed as a function of location.

Any tomographic solution may be used. Computed or time-of-flight tomography is performed. For example, a least squares computation is performed. A stop criterion or criteria representing a difference between the field of shifts as measured and a field of shifts calculated in a model based on distribution of sound speed in the tissue is used. The model simulates the propagation of acoustic energy or more directly the shifts from different receive apertures based on speed of sound by location. The model is varied to find the sound speed distribution matching the measured shifts. Other tomography solutions may be used. The computed tomography solution using least square fit solves for speed at different locations simultaneously. In an alternative embodiment, the magnitude of the shift of a location maps to a given speed of sound or difference in speed from a standard or assumed speed.

In one embodiment, the sound speed map is tomographically solved by dividing the scan area into N cells. The slowness (inverse of sound speed) is to be estimated inside each cell. For each cell, a delay is estimated by cross correlating beamformed signals from two receive sub-apertures but a same transmit aperture. This delay $\Delta t_i$, where i goes from 1 to N, is a result of sound speed differences along the receive paths from cell i to the centers of the two sub-apertures. Two rays from cell i to the centers of the two receive sub-apertures are formed. Each ray traverses different cells with different path lengths, resulting in $\Sigma_{j=1}^{N}(l_{1j}-l_{2j})\Delta s_j=\Delta t_i$, where $l_{1j}$ is the path length of the first ray across cell j, and $l_{2j}$ is the path length of the second ray across cell j. Many of the path lengths are zero. A matrix $\Delta L \Delta s = \Delta t$ is formed, allowing solving for $\Delta s^T=[\Delta s_1, \Delta s_2, \Delta s_3, \ldots \Delta s_N]$. The rank of the matrix is increased by repeating the steps above for different combination of sub-apertures.

The speed of sound at each of a plurality of locations is calculated. The speed for particular tissue of a specific patient is measured. The absolute sound speed for a one, two, or three-dimensional distribution of locations is found. Alternatively, a bulk sound speed is found. The speeds for locations in a region are averaged or otherwise combined to determine the bulk sound speed. In another approach, the tomographic solution solves for a bulk sound speed as one speed associated with multiple locations for which shifts are estimated.

In act 34, the image processor transmits the calculated speed or speeds. The transmission is to another component of the ultrasound system or out of the ultrasound system. For example, the speed is transmitted to a memory, beamformer, display, and/or network.

An image of the speed of sound may be generated and provided to the display. The image includes the speed as text, such as an alphanumeric representation of speed for a location or region of the patient. In one embodiment, a single speed of sound is determined. For example, a user positions a pointer on an image. In response, the ultrasound scanner outputs a speed of sound calculated for that point or a bulk speed of sound for a region around and including the point. A graph, color-coding, intensity, or other modulation by speed may be used. Alternatively, the image includes a spatial distribution of speeds of sound for different locations. A one, two, or three-dimensional representation of speed as a function of location is rendered to the display. The display grid may be different from or the same as the scan grid and/or grid for which displacements are calculated. Color, brightness, luminance, hue, or other characteristic of pixels is modulated as a function of the speed of sound. Variation in speed by region may be visualized.

The speed for a location or variation in speed over locations may be used as a biomarker. For example, the speed may indicate whether a liver includes fatty liver tissue. A fat fraction for the liver may be estimated from the speed and displayed as a value with or instead of the speed. The speed information may be presented or displayed with other information, such as B-mode and/or Doppler mode (e.g., color flow) scans, to assist in diagnosis.

In another example, a bulk speed or absolute speeds are transmitted to a beamformer. The speed is transmitted to the beamformer controller, receive beamformer, and/or transmit beamformer. Alternatively, the speed is used to determine a delay or phase profile, and the profile is transmitted to the beamformer. Rather than determining delay or phase shifts due to aberration without changing the speed of sound in beamformation, the speed of sound may be altered. Using the actual speed of sound or speeds of sound, the focusing and scan format of the beamformer is controlled to increase resolution or for more accurate scanning. For example, the speed of sound is assumed to be 1450 m/s, but the actual bulk speed of sound for the region of interest is 1540 m/s. The delay and/or phase profiles for beamforming are based on the speed of sound, so new profiles are calculated or looked up for the measured speed rather than the assumed speed. As a result, the point or line reflectors are more defined or less blurry than if the assumed speed were used. Using the actual speed of sound may improve a sonographer's ability to distinguish anatomy and/or tissue state, helping with diagnosis. The actual speed of sound also results in more reliable distance indication. Greater improvements may be provided for a beamformation model accounting for variations is speed by location.

FIG. 3 shows one embodiment of a system for estimating speed of sound in tissue. The system implements the method of FIG. 1 or other methods. Speed of sound is tomographically solved from axial displacements estimated from beamformed data of different receive apertures. The same transmit event is used to form the data, limiting or avoiding motion artifacts.

The system is a medical diagnostic ultrasound imaging system. In alternative embodiments, the system is a personal computer, workstation, PACS station, or other arrangement at a same location or distributed over a network for real-time or post acquisition imaging.

The system includes a transmit beamformer 12, a transducer 14, a receive beamformer 16, an image processor 18, a display 20, and a memory 22. Additional, different, or fewer components may be provided. For example, a user input is provided for manual or assisted designation of a region of interest for which information is to be obtained.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. The waveforms are generated and applied to elements of the transducer 14 with any timing or pulse repetition frequency. The transmit beamformer 12 may be configured to generate a sequence or other combination of excitation pulses for a region.

The transmit beamformer 12 connects with the transducer 14, such as through a transmit/receive switch. The electrical waveforms generated by the transmit beamformer 12 cause the transducer 14 to generate acoustic waves. Upon transmission of acoustic waves from the transducer 14, one or more focused beams are formed during a given transmit event. The transmit beams are focused in the region of interest. A sequence of transmit beams may be generated to scan a two or three-dimensional region. Sector, Vector®, linear, or other scan formats may be used. Broad beam, such as plane wave or diverging wave transmissions may be used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms and connects with the receive beamformer 16 for converting acoustic echoes into electrical signals. The transducer 14 transmits the acoustic waves. The waveforms are focused at a tissue region or location of interest in the patient and/or directed to cover all or part of the region of interest. The transmissions are angled relative to the transducer at any of various angles within a field of view of the transducer 14. For scanning with ultrasound to detect axial displacement, the transducer 14 transmits acoustic energy and receives echoes. Receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. Dynamic focusing on receive may be provided. Where only one depth or depth range is of interest, dynamic focusing may or may not be provided. The receive beamformer 16 outputs data representing spatial locations using the received acoustic signals. Relative delays and/or phasing and summation of signals from different elements provide beamformation.

For parallel receive beamformation, the receive beamformer 16 is a parallel receive beamformer configured to include additional sets of channels and corresponding summers. Each channel applies relative delays and/or phasing to form a beam with the summer. The receive beamformer 16 may have any number N of sets of channels and summers. N is an integer of 1 or greater for forming a corresponding number of beams simultaneously or in response to a same transmit. The receive beams may be formed as a regular sampling of space in a region of interest. The locations are simultaneously sampled by respective receive beams formed by the receive beamformer 16.

The receive beamformer 16 forms with two or more different receive apertures. Using parallel receive beamforming, at least one receive beam is formed for each aperture in response to the transmit. A set of channels forms each aperture. The apertures overlap (i.e., some elements or channels are included in both apertures) or are separate from each other. The receive beams from the different apertures represent the same scan line or scan lines, such as a same transmit scan line. Different sets of beamformed data are generated using the different apertures.

The receive beamformer 16 may include a filter, such as a filter for isolating information at a second harmonic or other frequency band relative to the transmit frequency band. Such information may more likely include desired tissue, contrast agent, and/or flow information.

For each receive aperture, the receive beamformer 16 outputs beam summed data representing one or more spatial locations. Data for a single location, locations along a line, locations for an area, or locations for a volume are output. Different sets of beamformed data representing the same locations responsive to the same transmit but different receive apertures are generated from the channel waveforms.

The image processor 18 or a separate beamformer controller configures the beamformers 12, 16. By loading values into registers or a table used for operation, the values of acquisition parameters used by the beamformers 12, 16 for transmitting and then receiving with different receive apertures are set. The values include delay or phase profiles that rely on the speed of sound. An assumed speed is used, but a previously determined speed or speeds may replace the assumed speed. For a given scan, the transmit beamformer 12 and/or the receive beamformer 16 use a given or default speed of sound. Any control structure or format may be used to establish the imaging. The beamformers 12, 16 are caused to acquire data for imaging at a frame rate and/or with a resolution. Different values of one or more acquisition parameters may result in a different frame rate and/or resolution.

The image processor 18 is an application specific integrated circuit, general processor, control processor, field programmable gate array, digital signal processor, analog circuit, digital circuit, combinations thereof, or other now known or later developed device for estimating shifts, calculating sound speed, generating an image showing sound speed, and/or controlling beamforming with the sound speed. The image processor 18 is configured by software, firmware, and/or hardware.

The image processor 18 is configured to determine a spatial or temporal shift for a location. The beamformed data from the different receive apertures is compared. The receive beams or parts of the receive beams are compared. A measure of similarity, such as cross-correlation, finds the shift along the depth dimension and/or axially along a same scan line. The amount of shift corresponding with the maximum or sufficient similarity between the data from the different apertures is selected or output. The shift is found for one or more locations. For each location, the location defines the data to be used from one set (e.g., window of 3-16 samples centered on the location) to compare to the data of the other set, with the location in the other set defining a starting point of the search.

The image processor 18 is configured to calculate the speed of sound in the tissue at the location based on the shift. The magnitude of the shift may be mapped to a change in the assumed speed or to a speed. In one embodiment, a set of shifts for respective different locations is used to tomographically solve for the speeds of sound at the different locations. A least squares solution may be used to tomographically solve for the speeds. Other tomographic solutions may be used.

The speed of sound is estimated for one location, such as a user designated location. Alternatively, the speed of sound is estimated for each of a plurality of locations. The image processor 18 determines a spatial distribution of speeds of sound in the patient.

The image processor 18 generates and outputs an image or display values mapped from the speed of sound to the display 20. A text or numerical indication of the speed of sound is displayed to the user. In one embodiment, the speed of sound is displayed as a function of location. Values, graphs, and/or tissue representations may be displayed using the speed at different locations. For a representation of the tissue, the speed of sound modulates the color, hue, brightness, and/or other display characteristic for different pixels representing a tissue region. The image processor 18 determines a pixel value (e.g., RGB) or a scalar value converted to a pixel value. The image is generated as the scalar or pixel values. The image may be output to a video processor, look-up table, color map, or directly to the display 20. The spatial distribution of speed in the tissue of the patient may be overlaid on another image, such as a B-mode image representing the anatomic structure or tissue.

The image processor 18 may provide additional information based on the sound speed. For example, a fat fraction ratio for liver tissue is determined, at least in part, from the bulk speed of sound for a region of the liver tissue. The fat fraction or other quantity derived from speed of sound is displayed to the user.

The display 20 is a CRT, LCD, monitor, plasma, projector, printer, or other device for displaying an image or sequence of images. Any now known or later developed display 20 may be used. The display 20 is operable to display one image or a sequence of images. The display 20 displays two-dimensional images or three-dimensional representations. The display 20 displays one or more images representing the speed of sound. A table, patient report, or tissue representation is displayed with the speed included. As another example, a speed of sound associated with a location indicated on a two-dimensional image or three-dimensional B-mode representation is displayed. Alternatively or additionally, the image is a graph. In yet other embodiments, a B-mode image overlaid with color modulation for a spatial distribution of speed of sound is displayed.

The image processor 18 may transmit the speed of sound to the transmit beamformer 12, the receive beamformer 16, or both. The transmission to the beamformers 12, 16 may be to a beamformer controller. The speed of sound value itself or the speed of sound as incorporated into delay/phase profiles based on the speed of sound are transmitted. The bulk speed of sound or absolute speeds for different locations are fed back to the beamformer controller to account for actual speed in beamformation. The beamformers 12, 16 are configured to scan using delay and/or phase profiles based on the speed of sound. Using the measured or actual speed of sound for the tissue of the patient to configure the beamformers 12, 16 may result in more accurate spatial representation. The estimated speed of sound is used for operating the beamformers 12, 16 in a subsequent scan of any type (e.g., B-mode imaging). The speed is estimated once for a given imaging session. In other embodiments, the speed is periodically estimated throughout an imaging session for a patient.

The image processor 18, beamformer controller, the receive beamformer 16, and the transmit beamformer 12 operate pursuant to instructions stored in the memory 22 or another memory. The instructions configure the system for performance of the acts of FIG. 1. The instructions configure the image processor 18, the beamformer controller, the receive beamformer 16, and/or the transmit beamformer 12 for operation by being loaded into a controller, by causing loading of a table of values, and/or by being executed.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for sound speed imaging, the method comprising:
    transmitting from elements of a transducer array, with an ultrasound scanner, acoustic energy into tissue of a patient;
    receiving acoustic echoes responsive to the transmitting with at least first and second sub-apertures of the elements used in the transmitting by the transducer array, the first sub-aperture formed of a different grouping of the elements than the second sub-aperture;
    for each of different locations, estimating a relative axial displacement of multiple signals of different depths from the received acoustic echoes of the first sub-aperture with multiple signals of different depths from the received acoustic echoes of the second sub-aperture;
    tomographically solving for speed of sound at each of the locations from the relative axial displacements; and
    generating an image of the speed of sound.

2. The method of claim 1 wherein the transmitting of the acoustic energy comprises transmitting the acoustic energy focused as a transmit beam along a scan line, and wherein the receiving of the acoustic echoes comprises receiving with dynamic focus for each of the first and second sub-apertures for the locations along the scan line.

3. The method of claim 1 wherein the transmitting of the acoustic energy comprises transmitting the acoustic energy as a plane wave, and wherein the receiving of the acoustic echoes comprises receiving for each of the first and second sup-apertures for the locations distributed in at least two dimensions.

4. The method of claim 1 wherein the receiving of the acoustic echoes comprises receiving with the first sub-aperture and the second sub-aperture sharing some of the elements.

5. The method of claim 1 wherein the estimating of the relative axial displacements comprises axially cross-correlating the signals from the received acoustic echoes of the first sub-aperture with the signals from the received acoustic echoes of the second sub-aperture.

6. The method of claim 1 wherein the estimating of the relative axial displacements comprises estimating time shifts.

7. The method of claim 1 wherein the estimating of the relative axial displacements comprises estimating the relative axial displacement along a transmit scan line as the axis.

8. The method of claim 1 wherein the tomographically solving for the speed of sound comprises solving with a least squares computation.

9. The method of claim 1 wherein the tomographically solving for the speed of sound comprises solving for an absolute speed of sound for each of the locations.

10. The method of claim 1 wherein the generating the image comprises generating an image of a spatial distribution of the speeds of sound for the patient for the locations.

11. The method of claim 1 wherein the generating the image comprises generating an image as including a value of the speed of sound.

12. The method of claim 1 further comprising using the speed of sound in a beamformer of the ultrasound scanner for imaging the patient.

13. The method of claim 1 wherein the generating the image comprises generating an image of a bulk speed of sound for a plurality of the locations.

14. The method of claim 1 wherein the estimating of the relative axial displacements comprises estimating with the signals from the received acoustic echoes of the first and second sub-apertures comprising receive beamformed signals.

15. The method of claim 14 wherein the receive beamformed signals comprise (1) radio frequency or (2) in-phase and quadrature signals.

16. A method for imaging speed of sound, the method comprising:
    generating a transmitted field with elements of a transducer array of an ultrasound system;
    recording scattered waves from the transmitted field with multiple spatially overlapped receive sub-apertures of the elements of transducer array, the elements for the overlapped receive sub-apertures sub-apertures used to generate the transmitted field;
    forming multiple sets of beamformed data from the scattered waves for the multiple spatially overlapped receive sub-apertures, respectively;
    estimating relative axial spatial displacements or relative temporal displacements between the multiple sets of the beamformed data, each of the displacements being estimated from beamformed data for multiple depths for each of the sets;
    calculating speed of sound from the displacements; and
    displaying an image of the speed of sound.

* * * * *